(12) United States Patent
Michel et al.

(10) Patent No.: US 6,945,955 B1
(45) Date of Patent: Sep. 20, 2005

(54) SENSOR SYSTEM INCLUDING A PORT BODY

(75) Inventors: Willy Michel, Burgdorf (CH); Ulrich Haueter, Grosshöchstetten (CH); Thomas Frei, Lützelflüh (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 09/314,919

(22) Filed: May 19, 1999

(30) Foreign Application Priority Data

May 20, 1998 (DE) .................. 198 22 771

(51) Int. Cl.⁷ ............................................. A61M 31/00
(52) U.S. Cl. .................................................. 604/93.01
(58) Field of Search ............................ 604/27, 43, 93,
604/174, 175, 506, 96.01, 104, 164.1, 913;
600/367, 362, 573, 579, 363, 576; 606/201,
606/202

(56) References Cited

U.S. PATENT DOCUMENTS

| | | | | |
|---|---|---|---|---|
| 4,799,494 A | * | 1/1989 | Wang ........................... | 600/566 |
| 4,955,861 A | | 9/1990 | Enegren et al. | |
| 5,033,476 A | * | 7/1991 | Kasai .......................... | 604/576 |
| 5,279,610 A | * | 1/1994 | Park et al. ................... | 606/108 |
| 5,281,199 A | * | 1/1994 | Ensminger et al. .......... | 604/93 |
| 5,286,453 A | * | 2/1994 | Pope ........................... | 600/576 |
| 5,306,255 A | | 4/1994 | Haindl | |
| 5,330,498 A | * | 7/1994 | Hill ............................. | 606/194 |
| 5,337,756 A | * | 8/1994 | Barbier et al. .............. | 600/576 |
| 5,366,478 A | * | 11/1994 | Brinkerhoff et al. ........ | 660/213 |
| 5,391,156 A | * | 2/1995 | Hildwein et al. ........... | 604/174 |
| 5,480,410 A | * | 1/1996 | Cuschieri et al. ........... | 606/213 |
| 5,514,133 A | * | 5/1996 | Golub et al. ................. | 606/1 |
| 5,522,791 A | * | 6/1996 | Leyva ......................... | 600/207 |
| 5,545,143 A | | 8/1996 | Fischell | |
| 5,607,390 A | * | 3/1997 | Patsalos et al. .............. | 604/29 |
| 5,674,196 A | * | 10/1997 | Donaldson et al. .......... | 604/93 |
| 5,741,298 A | * | 4/1998 | Macleod ..................... | 606/213 |
| 5,906,577 A | * | 5/1999 | Beane et al. ................. | 600/207 |
| 5,954,687 A | * | 9/1999 | Baudino ....................... | 604/48 |
| 6,010,494 A | | 1/2000 | Schafer ....................... | 604/533 |
| 6,053,902 A | | 4/2000 | Bestetti et al. .............. | 604/523 |
| 6,152,933 A | * | 11/2000 | Werp et al. .................. | 606/130 |
| 6,270,475 B1 | | 8/2001 | Bestetti et al. ........... | 604/93.01 |
| 6,770,070 B1 | * | 8/2004 | Balbierz ....................... | 606/41 |

FOREIGN PATENT DOCUMENTS

DE    3742263    12/1987
EP    0302076    4/1987

* cited by examiner

Primary Examiner—Manuel Mendez
(74) Attorney, Agent, or Firm—Dorsey & Whitney LLP

(57) ABSTRACT

The invention provides a device and methods for analysing body fluids wherein the device is implanted in the body and provides for both the delivery of substances into the body and for the testing of body fluids.

8 Claims, 1 Drawing Sheet

SENSOR SYSTEM INCLUDING A PORT BODY

RELATED APPLICATIONS

This application claims the priority of German Patent Application No. 198 22 711.6, filed May 20, 1998, which is incorporated herein by reference.

BACKGROUND

The invention relates to a process and a device for accessing and analysing body fluids. More particularly, it relates to an implantable device for providing access to the interior of the body and for providing for detecting the concentration and/or existence of substances in body fluids, wherein the device provides a vehicle for both delivery of substances into the body and for analysing of body fluids. The invention encompasses various embodiments wherein the body fluids may be analysed in situ, or partially or completely extracted or aspirated for analysis.

A number of procedures exist in medicine for detecting the concentration and/or existence of substances in body fluids. When testing for blood sugar concentration, for instance, there is the option on the one hand of piercing the patient's skin, such as on a finger, for testing the blood sugar content of blood drawn in this manner. Virtually any intercellular fluid may be examined in many different ways and for different characteristics using a selected "test strip" after such a fluid has been obtained. Another piercing procedure involves piercing the skin with needles for introducing and/or retrieving a sensor at a test point in the body.

However, a severe disadvantage or drawback of such invasive techniques is that they are generally unpleasant experiences to the patient. Another related drawback is that a piercing may be required for each desired test, and such piercings may be frequent and repeated. In addition, needle-type sensors will fail due to being affected and/or rejected by the body after a very short time (approximately half a day).

Non-invasive techniques, for instance detecting said concentration by fluoroscopic methods, have not yet been adequately developed to obtain sufficiently accurate values.

Port bodies, implanted subcutaneously or percutaneously and used for administering drugs through tubular channels, are known from at least U.S. Pat. No. 5,306,255 and EP 0 302 076.

SUMMARY

The present invention provides an implantable device for providing access to the interior of the body and for providing for detecting the concentration and/or existence of substances in body fluids, wherein the device provides a vehicle for both delivery of substances into the body and for analysing of body fluids.

It is an object of the invention to provide a method and a device for detecting the concentration and/or existence of substances in body fluids by which the disadvantages of the devices and methods described above are overcome as far as possible. Another object of the present invention is to help avoid pain and inconvenience for patients.

The invention provides a device and method for analysing body fluids wherein the body fluids are accessed via an access means implanted in the body.

The inventive method for detecting the concentration and/or existence of substances in body fluids attains this object by accessing the interior of the body and any fluids to be analysed by an access means implanted permanently or semi-permanently in the body.

Many patients needing regular medication due to the concentrations of certain substances in their body fluids being too low or too high, are being administered the regular medication through an implanted, artificial access means providing access to the interior of their body. The process according to the invention has an object of using such implanted access means for gaining access to body fluids so the fluids can be analysed. Access means, which may comprise quick-replacement elements such as a framed sealing diaphragm, may be permanently or semi-permanently implanted in the body, and include structures or features which end at parts of the body where no blockage of the endings will occur for some length of time. Such access means may be designed to ensure that attacks by rejection mechanisms of the body or attacks by body cells will not affect their function at least over a predetermined period of use. According to the present invention, these aspects of typical access means may now also be used for accessing body fluids. It is an advantage of the present invention that permanent or semi-permanent implanted access means may be used to allow access to body fluids for analysis over an extended period of time and/or to allow for repeated sampling or analysis of body fluids, while sparing a patient the discomfort of repeated piercings.

According to one embodiment of the present invention, access to a body fluid may be effected through a permanently or semi-permanently implanted device for administering medicaments and, in a preferred embodiment, through a port body implanted in the skin, wherein the port body comprises a tubular arrangement extending into the interior of the body.

In one embodiment, a port body is suitable as a permanent means of access for administering insulin, and is implanted into the umbilical vein within the abdominal cavity of the body. The abdominal cavity, the peritoneum and the umbilical vein have proven to be advantageous sites for the administration of insulin, due to insulin being resorbed faster there than after subcutaneous administration. Owing to the fact that insulin consumption takes place in the body cells as such, the cell fluid also seems a suitable place to measure the blood sugar content, due to measuring a central average in this case directly at the place of consumption. Accordingly, port bodies according to the present invention are suitable for the administration of insulin into the abdominal cavity and as access points to body fluid to be analysed.

Although said port bodies are invasive devices, one-time implantation typically will be sufficient, whereby, in a port body in accordance with the present invention, a patient no longer must experience the pain and inconvenience of subsequent repeated access to body fluids for testing purposes.

One embodiment of the process according to the invention is characterized by a test sensor being introduced into the interior of the body through the access means for detecting the concentration and/or existence of substances, with detection being performed at that point. This creates a chance for continuous and intermittent testing, whereby the sensor remains at the test site in the interior of the body and is introduced via a separate tube when using a port body comprising a tubular system.

In another embodiment of the invention, a test sensor remaining in the interior of the body takes body fluid from the interior of the body through the access means, followed by analysis at a point remote from the point of retraction. Body fluid is still analysed, for instance, within the body, preferably at an intermediate point of the tubular system, by means of a sensor and is aspirated for this purpose to a selected point. The benefit of using an intermediate point as a test site is that any deposits, which might arise at the end of the tube, by which access may be effected, will not have any negative influence on the accuracy of tests. Also, the tubular section between the ends, both interior and exterior, protects a test sensor provided at an intermediate point of the tube against direct contamination. Further, constancy of temperature is ensured. When the sensor is replaced, the abdominal cavity is not affected.

According to an alternative embodiment of the process according to the invention, body fluids may naturally be aspirated away or extracted from the body for analysis.

In addition, a preferred embodiment of the invention uses a dialysis microprobe by which substances are extracted from body fluids.

The device for detecting the concentration and/or existence of substances in body fluids according to the invention comprises an access means to the interior of the body, permanently or semi-permanently implanted in the body, and adapted for allowing access through said access means to body fluids for analysis thereof, in situ. In other embodiments of the present invention, the body fluids may be aspirated to a selected point with in the access means for analysis, or they may be removed completely from the body and access means for analysis at a remote location.

Preferably, in one embodiment, the access means is a permanently implanted device for administering medicaments, in particular a port body implanted into the skin, comprising a tubular system extending into the interior of the body. Such a port body may be implanted subcutaneously, as well.

The access means or port body of the present invention comprises tubes, passages or pathways by means of which a test sensor may be introduced into the interior of the body or to a selected location along the passages or pathways. The access means preferably comprises a separate tube for the introduction of a sensor.

One preferred design of the device according to the invention is characterized in that the access means is associated with a dialysis microprobe through which substances in body fluids are withdrawn. The microprobe may be either permanently or removably associated with the access means.

Furthermore, the invention refers to the use of an access means to the interior of the body, permanently or semi-permanently implanted in the body, through which the concentration and/or existence of substances in body fluids are detected and/or analysed.

Other objects, features, embodiments and advantages of the device and method of the present invention will become more fully apparent and understood with reference to the following description and appended drawings and claims.

DETAILED DESCRIPTION

The accompanying Figures and this description depict and describe embodiments of the port body and methods of the present invention, and features and components thereof. With regard to means for fastening, mounting, attaching or connecting the components of the present invention to form the device as a whole, unless specifically described otherwise, such means are intended to encompass conventional fasteners such as threaded connectors, snap rings, clamps such as screw clamps and the like, rivets, toggles, pins and the like. Components may also be connected by adhesives, glues, welding, ultrasonic welding, and friction fitting or deformation, if appropriate. Unless specifically otherwise disclosed or taught, materials for making components of the present invention may be selected from appropriate materials such as metal, metallic alloys, natural and manmade fibers, vinyls, plastics and the like, and appropriate manufacturing or production methods including casting, extruding, molding and machining may be used.

Any references to front and back, right and left, top and bottom and upper and lower are intended for convenience of description, not to limit the present invention or its components to any one positional or spacial orientation.

Figure 1:
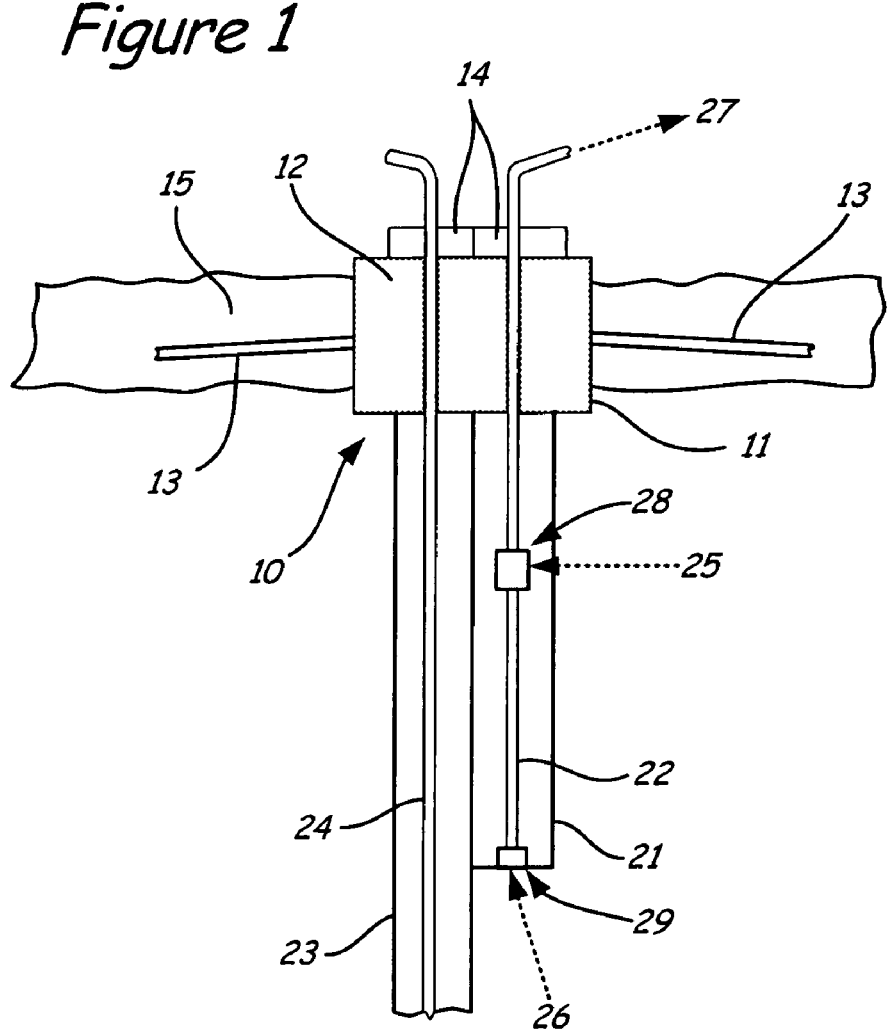
FIG. 1 depicts an implanted port body adapted according to the present invention.

Referring then to FIG. 1, a port body 10, an implantable or partially implantable device for operably coupling a conduit or hose outside of a human or animal body to a catheter, hose, conduit or the like inside the body, is shown implanted in the skin 15 of a patient (human, animal, etc.). The port body 10 comprises a shaft section 11 to which an approximately disc-shaped anchoring section 13 is attached, acting as an anchor or attachment for anchoring, attaching and/or stabilizing the port body 10 in (or under) the skin.

The shaft section 11 forms a hollow enclosure containing and/or supporting an elastic self-closing diaphragm 12.

Separate tubes extend generally perpendicularly away from the innermost, lower end of the port body 10, including a feed tube 23 (the full length of which is not shown) and a shorter aspiration tube 21. A feed catheter 24 and an aspiration catheter 22 may be introduced through the diaphragm 12 into each of the tubes 23 and 21, respectively. Although the tubes are shown as extending perpendicularly away from the port body 10, they may extend away therefrom at another angle. Also, in some situations, a port body may have more than two associated tubes, and the tubes 23, 21 may be adapted to contain more than one catheter each.

The tube 23, either the mouth thereof or a point or points along the tube 23, is supplied with a drug, such as insulin, through the feed catheter 24, whilst from a point or points adjacent to or at the end of the tube 21, e.g., at its open mouth, body fluids may be withdrawn through the aspiration catheter 22.

FIG. 1 shows fastening sections 14 at the top of the shaft 11, provided for connection of the upper sealing and/or closing caps of the catheters 24 and 22, not shown in the Figure.

The feed tube 23 is preferably of a standard length of 150 or 180 mm, whilst the aspiration tube 21 presumably has an approximate minimum length of 30 mm, preferably 60 to 120 mm, possibly even 180 mm. This arrangement therefore clearly shows that this port body may be used both for the supply of drugs through the feed catheter 24 and for access to body fluids through the aspiration catheter 22. The tubes 23 and 21 preferably extend into the patient's abdominal cavity where cell fluid can be found, which may be provided with a drug or analysed for specific concentrations.

The dashed arrows show selected various test sites for testing the concentration or existence of certain substances. For example, a sensor 28 may be applied to test point 25 where fluid is aspired from the bottom end of the catheter 22 somewhat upwards, in order to perform a test precisely at this intermediate point 25. As described above, a sensor 28 attached at point 25 would be protected against deposits by the lower section of the tube 21 and/or the catheter 22.

When a test is performed at a point where no major deposits are to be expected, a test sensor 29 may also be attached permanently or removably at a point marked by the dashed arrow 26. The benefit of this detection method lies in the fact that aspiration is no longer required and detection will be feasible directly at a specified test point.

In the two embodiments described, where the test sensor remains permanently in the tube 25 and/or on the end of the tube 26, an electronic test sensor is used, the connecting wires of which may be routed out of the body together with the catheter 22.

Typically, electronic test sensors suitable for use in the present invention comprise a working electrode, a counterelectrode and a zero-current reference electrode. When the shaft 11 of the port body is of a metallic material, the shaft 11 may be used as a reference electrode or counterelectrode, thus allowing simplification of the electric sensor during the said tests according to the invention.

Another option for using the arrangement shown in the Figure consists of inserting a probe (not shown) through the tube 21 for one-time testing or for each individual test. In this embodiment, the probe may comprise a test strip for detecting a concentration. Taking and evaluation of a reading may be performed in inserted condition or after removal.

According to the present invention, a fluid may be aspirated or removed from the interior of the body through the catheter 22 and, as depicted by the dashed arrow 27, analysed at a remote laboratory.

Figure 2:
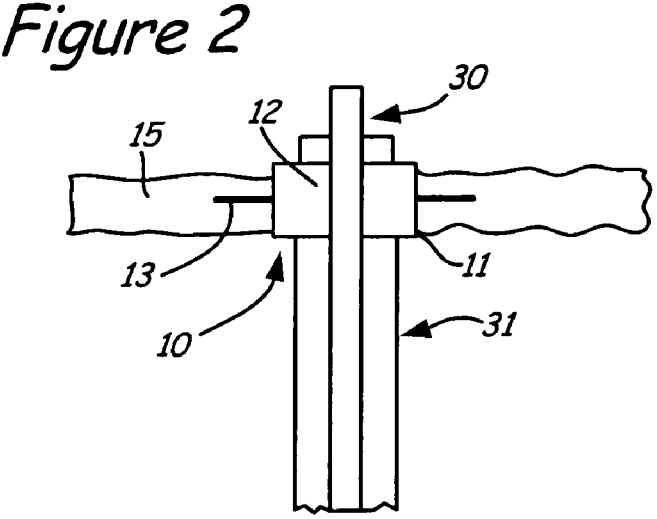
FIG. 2 depicts an implanted port body with a microdialysis probe according to the present invention.

Another option for using the arrangement is shown in FIG. 2, in which the invention may use a microdialysis probe 30, inserted through a tube 31, to extract substances from body fluids. This probe can be used alone, or in conjunction with a feed tube and catheter.

In the foregoing description embodiments of the invention have been presented for the purpose of illustration and description. They are not intended to be exhaustive or to limit the invention to the precise form disclosed. The embodiments were chosen and described to provide an illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A method of analyzing subject fluids and providing substances to the subject fluids comprising the steps of:
    (a) accessing a site through an elastic self closing diaphragm implanted in the skin of a living body;
    (b) delivering a substance to the site via a feed element associated with the elastic self closing diaphragm; and
    (c) analyzing the subject fluids via an aspiration element associated with the elastic self closing diaphragm.

2. The method of claim 1 further comprising the step of extracting the subject fluids via the aspiration element.

3. The method of claim 1 further comprising the step of inserting an analysis element via the aspiration element.

4. The method of claim 3 further comprising the substep of inserting the analysis element to a midpoint of the aspiration element.

5. The method of claim 3 further comprising the substep of inserting to a distal end of the aspiration element.

6. The method of claim 3 further comprising the substep of inserting the analysis element via the aspiration element into the site, the analysis element being disposed externally to the aspiration element.

7. The method of claim 3 wherein the analysis element is a sensor.

8. The method of claim 3 wherein the analysis element is a probe.

* * * * *